United States Patent
Norris et al.

(10) Patent No.: US 10,925,581 B2
(45) Date of Patent: Feb. 23, 2021

(54) INTRAVASCULAR DEVICE WITH CAPTIVELY-HELD FILLING

(71) Applicant: Koninklijke Philips N.V., Amsterdam (NL)

(72) Inventors: Danielle Norris, San Diego, CA (US); Gloria Robinson, San Diego, CA (US); Natalie Yakos, San Diego, CA (US); Christopher LeBlanc, Carlsbad, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1304 days.

(21) Appl. No.: 15/148,421

(22) Filed: May 6, 2016

(65) Prior Publication Data
US 2016/0324503 A1    Nov. 10, 2016

Related U.S. Application Data

(60) Provisional application No. 62/158,757, filed on May 8, 2015.

(51) Int. Cl.
*A61B 8/00* (2006.01)
*A61B 8/12* (2006.01)

(52) U.S. Cl.
CPC ............ *A61B 8/445* (2013.01); *A61B 8/12* (2013.01); *A61B 8/4281* (2013.01); *A61B 8/4461* (2013.01); *A61B 2562/12* (2013.01)

(58) Field of Classification Search
CPC ......... A61B 8/445; A61B 8/12; A61B 8/4281; A61B 8/4461; A61B 2562/12
See application file for complete search history.

(56) References Cited

U.S. PATENT DOCUMENTS

| | | | |
|---|---|---|---|
| 5,243,988 A | 9/1993 | Sieben | |
| 5,372,138 A * | 12/1994 | Crowley | ............... A61B 5/416 600/463 |
| 5,400,785 A | 3/1995 | Crowley | |
| 5,546,948 A | 8/1996 | Hamm | |
| 8,104,479 B2 | 1/2012 | Glynn | |
| 2008/0312536 A1 | 12/2008 | Dala-Krishna | |
| 2011/0237955 A1 | 9/2011 | Dietz | |
| 2014/0257105 A1 | 9/2014 | Dausch | |

* cited by examiner

*Primary Examiner* — Peter Luong

(57) ABSTRACT

Intravascular systems, devices, and methods having a captively-held filling are provided. An intravascular imaging device can include a flexible elongate member including a lumen having a proximal portion and a distal portion; a drive cable disposed within the lumen such that an ultrasound transducer coupled to the drive cable is positioned within the distal portion of the lumen; and a filling captively held within at least the distal portion of the lumen and surrounding the ultrasound transducer, the filling facilitating transmission and receipt of ultrasound signals. A method of manufacturing an intravascular imaging device can include acquiring a flexible elongate member including a lumen; inserting a drive cable into the lumen, a rotational ultrasound transducer being coupled to the drive cable; inserting a filling that facilitates transmission and receipt of ultrasonic signals into the lumen such that the filling surrounds rotational ultrasound transducer; and sealing the filling within the lumen.

15 Claims, 14 Drawing Sheets

INTRAVASCULAR DEVICE WITH CAPTIVELY-HELD FILLING

CROSS REFERENCE TO RELATED APPLICATIONS

The present application claims priority to and the benefit of the U.S. Provisional Patent Application No. 62/158,757, filed May 8, 2015, which is hereby incorporated by reference in its entirety.

TECHNICAL FIELD

The present disclosure relates generally to intravascular devices and, in particular, to catheters that have a pre-filled lumen that minimizes the difficulties associated with flushing the catheter prior to use.

BACKGROUND

Minimally invasive sensing systems are routinely utilized by medical professionals to evaluate, measure, and diagnose conditions within the human body. As one example, intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device includes one or more ultrasound transducers arranged at a distal end of an elongate member. The elongate member is passed into the vessel thereby guiding the transducers to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. The transducer element is oriented such that the ultrasound beam propagates generally perpendicular to the axis of the device. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

The spinning transducer and driveshaft of a rotational IVUS device are positioned within the sheath to protect the vessel tissue from damage. (In contrast, solid-state IVUS devices have no rotating mechanical element and an array of ultrasound transducers distributed around the circumference of the device can be placed in direct contact with the blood and vessel tissue with minimal risk of vessel trauma.) Ultrasonic signals do not propagate well through air. If the sheath were only filled with air, the IVUS image of the vessel would be distorted and have limited diagnostic value. Thus, a user, such as a physician or other medical professional, always performs a preparation step of filling the space between the sheath and the transducer with saline prior to using the transducer to image the vessel. This step is generally referred to as flushing. Conventionally, intravascular devices have an entry port at the proximal end that is used to inject the saline. Flushing eliminates air bubbles in the space between the sheath and transducer, which can degrade or inhibit image quality. However, performing this preparation step prior to the imaging procedure requires the user's time and attention. Sometimes, the user needs to re-flush, which interrupts the imaging procedure. Flushing may also be difficult to perform because the gap between the drive cable and the sheath is small. Further, the design options for rotational IVUS devices, particularly at the proximal end, are limited by the need to include components for flushing.

Accordingly, there remains a need for intravascular devices, systems, and methods that preserve or improve IVUS image quality while eliminating difficulties associated with flushing.

SUMMARY

Some embodiments of the present disclosure are directed to an intravascular device having a sealed lumen with a filling (e.g., saline, ultrasound gel, etc.) that facilitates ultrasound data collection. A drive cable, with an intravascular ultrasound (IVUS) transducer attached at a distal end, is positioned within the lumen. The lumen is filled, e.g., during manufacture, with the filling so that the IVUS transducer is surrounded. The filling can improve collection of ultrasound data and generation of high quality images of a patient's blood vessel. An IVUS imaging procedure is more efficient because a user, such as a physician or other medical professional, does not have to flush the lumen with a fluid before starting the procedure.

In one exemplary implementation, an intravascular imaging device is provided. The intravascular imaging device includes a flexible elongate member including a lumen having a proximal portion and a distal portion; a drive cable disposed within the lumen such that an ultrasound transducer coupled to the drive cable is positioned within the distal portion of the lumen; and a filling captively held within at least the distal portion of the lumen and surrounding the ultrasound transducer, the filling facilitating transmission and receipt of ultrasound signals.

In one aspect of the present disclosure, the intravascular imaging device further includes a sealing element disposed within the lumen to captively hold the filling within the distal portion of the lumen. In one aspect, the drive cable extends through the sealing element. In one aspect, the drive cable is configured to rotate within the lumen. In one aspect, the sealing element comprises an o-ring or a bearing. In one aspect, the filling is captively held within the proximal and distal portions of the lumen. In one aspect, the filling comprises a solid, a liquid, a polymer, or a gel. In one aspect, the filling comprises saline or ultrasound gel. In one aspect, at least a portion of the flexible elongate member is formed of a material permeable to the filling such that the filling fills at least the distal portion of the lumen and surrounds the ultrasound transducer after the at least a portion of the flexible elongate member is positioned in the filling.

In one exemplary implementation, an intravascular imaging device is provided. The intravascular imaging device includes a flexible elongate member including a first lumen having a proximal portion and a distal portion; a sealing element disposed within the first lumen between the proximal and distal portions to isolate the proximal and distal portions; and a second lumen in fluid communication with the distal portion of the first lumen; and a drive cable disposed within the first lumen such that an ultrasound transducer coupled to the drive cable is positioned within the distal portion of the first lumen.

In one aspect of the present disclosure, the drive cable is configured to rotate within the first lumen, and wherein the sealing element is positioned relative the drive cable to permit rotation of the drive cable and to hold a filling captive within the distal portion of the first lumen. In one aspect, the second lumen extends from a proximal section of the flexible elongate member to the distal portion of the first lumen. In one aspect, the second lumen extends from a distal section of the flexible elongate member to the distal portion of the first lumen. In one aspect, the second lumen extends from an imaging window of the flexible elongate member to the distal portion of the first lumen. In one aspect, the intravascular imaging device further includes a third lumen in fluid communication with the distal portion of the first lumen.

In one exemplary implementation, a method of manufacturing an intravascular imaging device is provided. The method includes acquiring a flexible elongate member including a lumen; inserting a drive cable into the lumen, a rotational ultrasound transducer being coupled to the drive cable; inserting a filling that facilitates transmission and receipt of ultrasonic signals into the lumen such that the filling surrounds rotational ultrasound transducer; and sealing the filling within the lumen.

In one aspect of the present disclosure, the inserting a filling includes introducing a solid, a liquid, a polymer, or a gel into a distal portion of the lumen. In one aspect, the inserting a filling includes introducing a solid, a liquid, a polymer, or a gel into proximal and distal portions of the lumen. In one aspect, the sealing the filling includes positioning a sealing element around the drive cable. In one aspect, the sealing element includes an o-ring or a bearing. In one aspect, the inserting a filling includes introducing the filling into a distal portion of the lumen via a further lumen of the flexible elongate member, wherein a sealing element is positioned between the distal and a proximal portion of the lumen to isolate the distal and proximal portions. In one aspect, the sealing the filling includes introducing the filling into the distal portion of the lumen via a check valve disposed within the further lumen or positioning a plug within further lumen. In one aspect, the inserting a filling includes positioning at least a portion of the flexible elongate member in the filling, the at least a portion of the flexible elongate member being formed of a permeable material such that the filling surrounds the ultrasound transducer.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
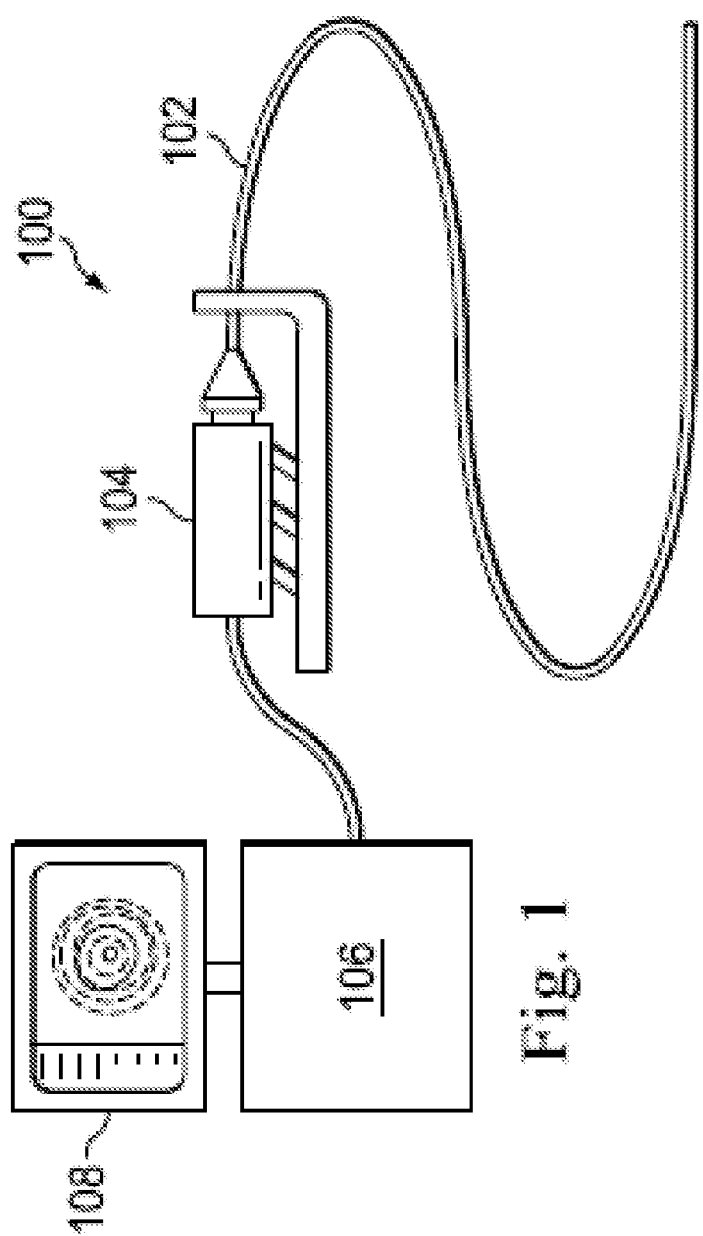
FIG. 1 is a diagrammatic schematic view of an intravascular imaging system according to an embodiment of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one or more implementations may be combined with the features, components, and/or steps described with respect to other implementations of the present disclosure. For simplicity, in some instances the same reference numbers are used throughout the drawings to refer to the same or like parts.

Some embodiments of the present disclosure relate generally to intravascular imaging devices, systems and methods having a lumen with a captive filling. The filling, such as saline, ultrasound gel, etc., facilitates transmission of ultrasound signals and reception of ultrasound echoes. A drive cable, with an intravascular ultrasound (IVUS) transducer coupled thereto, is positioned within the lumen such that the filling surrounds at least the transducer. The filling can be disposed within the distal portion of the lumen or within both proximal and distal portions of the lumen. The filling is captively maintained within the lumen by a sealing element (e.g., an o-ring, a bearing, etc.) positioned within the lumen. The sealing element both prevents the filling from leaking and allows the drive cable to rotate. Other embodiments of the present disclosure include a further lumen in fluid communication directly with a distal portion of the lumen in which the IVUS transducer is positioned. Thus, a user need only fill the distal portion of the lumen, rather than the entire lumen.

The devices, systems, and methods of the present disclosure provide numerous advantages. Utilizing an intravascular imaging device with a pre-filled imaging core lumen may reduce the set up time and/or total time for an imaging procedure. For example, a user does not need to flush the intravascular device prior to the imaging procedure and/or reflush the device during the procedure. Intravascular devices of the present disclosure can also provide high quality IVUS images because there are no bubbles within the imaging core lumen. The imaging core lumen can be pre-filled with a variety of substances, such as ultrasound gel, which are not conventionally used for flushing. The imaging core lumen can be sealed such that it is less likely for air bubbles to be deposited into the blood stream. A medical services provider, such as a hospital or catheterization lab, can also stock fewer supplies because flushing fluid is no longer needed. Similarly, an intravascular device manufacturer may need not ship accessories associated with flushing with each intravascular device. Manufacturers face fewer design constraints because components for flushing need not be included in the intravascular device.

Referring to FIG. 1, shown therein is an IVUS imaging system 100 according to an embodiment of the present disclosure. In some embodiments of the present disclosure, the IVUS imaging system 100 is a rotational IVUS imaging system. In that regard, the main components of the rotational IVUS imaging system are the rotational IVUS catheter 102, a patient interface module (PIM) and/or rotational pullback device 104, an IVUS console or processing system 106, and a monitor 108 to display the IVUS images generated by the IVUS console 106.

Figure 2:
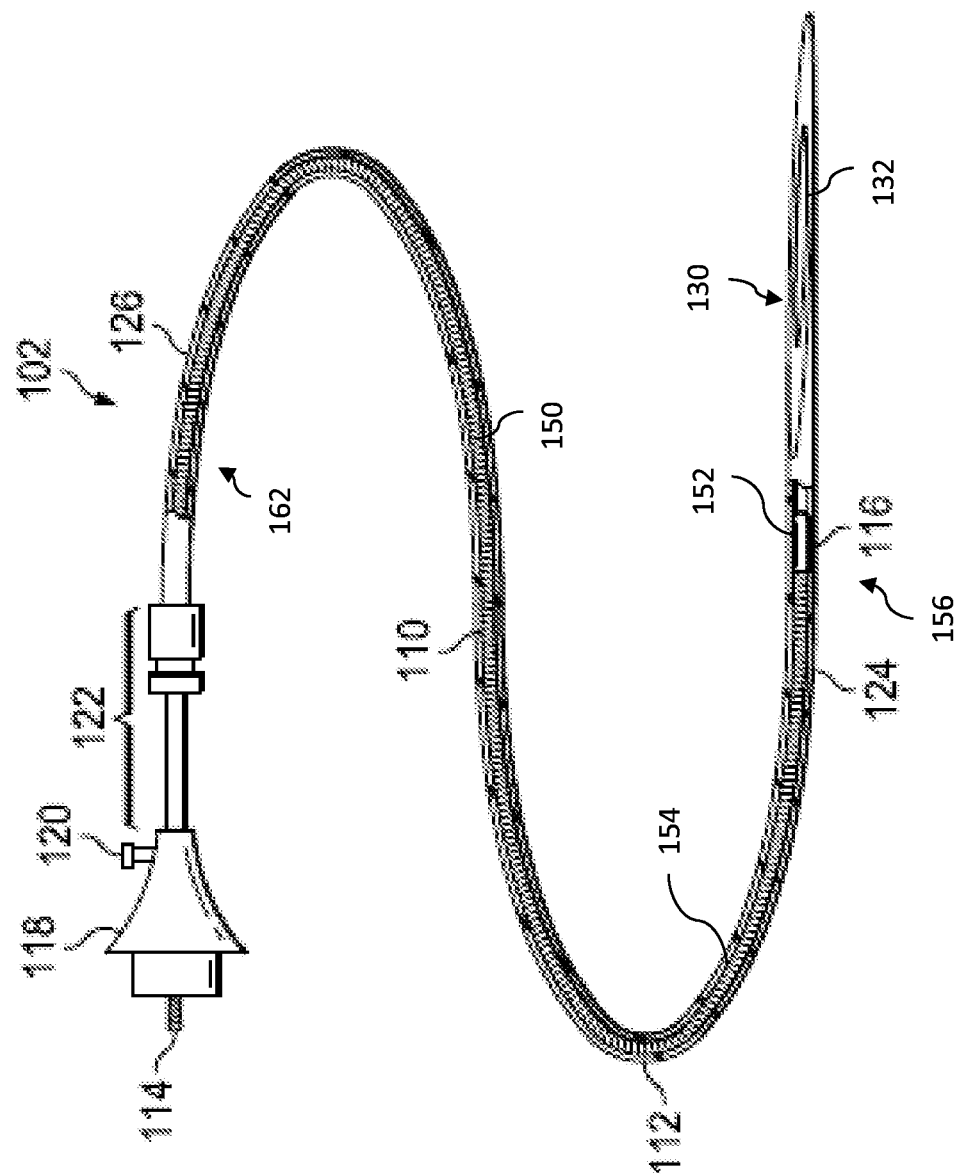
FIG. 2 is a partial cutaway, perspective view of an intravascular device according to an embodiment of the present disclosure.

Referring now to FIG. 2, shown therein is a diagrammatic, partial cutaway perspective view of the rotational IVUS catheter 102 according to an embodiment of the present disclosure. In that regard, FIG. 2 shows additional detail regarding the construction of the rotational IVUS catheter 102. In many respects, this catheter is similar to traditional rotational IVUS catheters, such as the Revolution® catheter available from Volcano Corporation and described in U.S. Pat. No. 8,104,479, or those disclosed in U.S. Pat. Nos. 5,243,988 and 5,546,948, each of which is hereby incorporated by reference in its entirety. The rotational IVUS catheter 102 includes an imaging core 110 and an outer catheter/sheath assembly 112. The outer catheter/sheath assembly 112 can be described as a flexible elongate member. The imaging core 110 includes a flexible drive shaft or drive cable 150 that is terminated at the proximal end by a rotational interface 114 providing electrical and mechanical coupling to the PIM and/or rotational pullback device 104 of FIG. 1. The distal end of the flexible drive shaft 150 of the imaging core 110 is coupled to a housing 116 containing the ultrasound transducer 152 and, in some instances, associated circuitry.

The catheter/sheath assembly 112 includes a hub 118 that supports the rotational interface and provides a bearing surface and a fluid seal between the rotating and non-rotating elements of the catheter assembly. In some embodiments of the present disclosure (as shown in and described with respect to, e.g., FIGS. 6 and 7), the hub 118 includes a luer lock flush port 120 through which saline or other biocompatible and ultrasound-compatible fluid is injected to flush out the air and fill the inner lumen 154 of the sheath 112 at the time of use of the catheter 102. The saline or other fluid also acts a lubricant for the rotating driveshaft 150. The hub 118 is coupled to a telescope 122 that includes nested tubular elements and a sliding fluid seal that permit the catheter/sheath assembly 112 to be lengthened or shortened to facilitate axial movement of the transducer housing 116 within an acoustically transparent window 124 of the distal portion of the catheter 102. In some embodiments, the window 124 is composed of thin-walled plastic tubing fabricated from material(s) that readily conduct ultrasound waves between the transducer and the vessel tissue with minimal attenuation, reflection, or refraction. A proximal shaft 126 of the catheter/sheath assembly 112 bridges the segment between the telescope 122 and the window 124, and is composed of a material or composite that provides a lubricious internal lumen and optimum stiffness, but without the need to conduct ultrasound. A distal shaft 156 of the catheter/sheath assembly 112 includes the window 124. In the embodiment of FIG. 2, a distal portion 130 of the flexible elongate member 112 includes a rapid-exchange port 132 configured to receive a guidewire utilized to guide advancement of the catheter 102 to a desired location within a patient.

Figure 3:
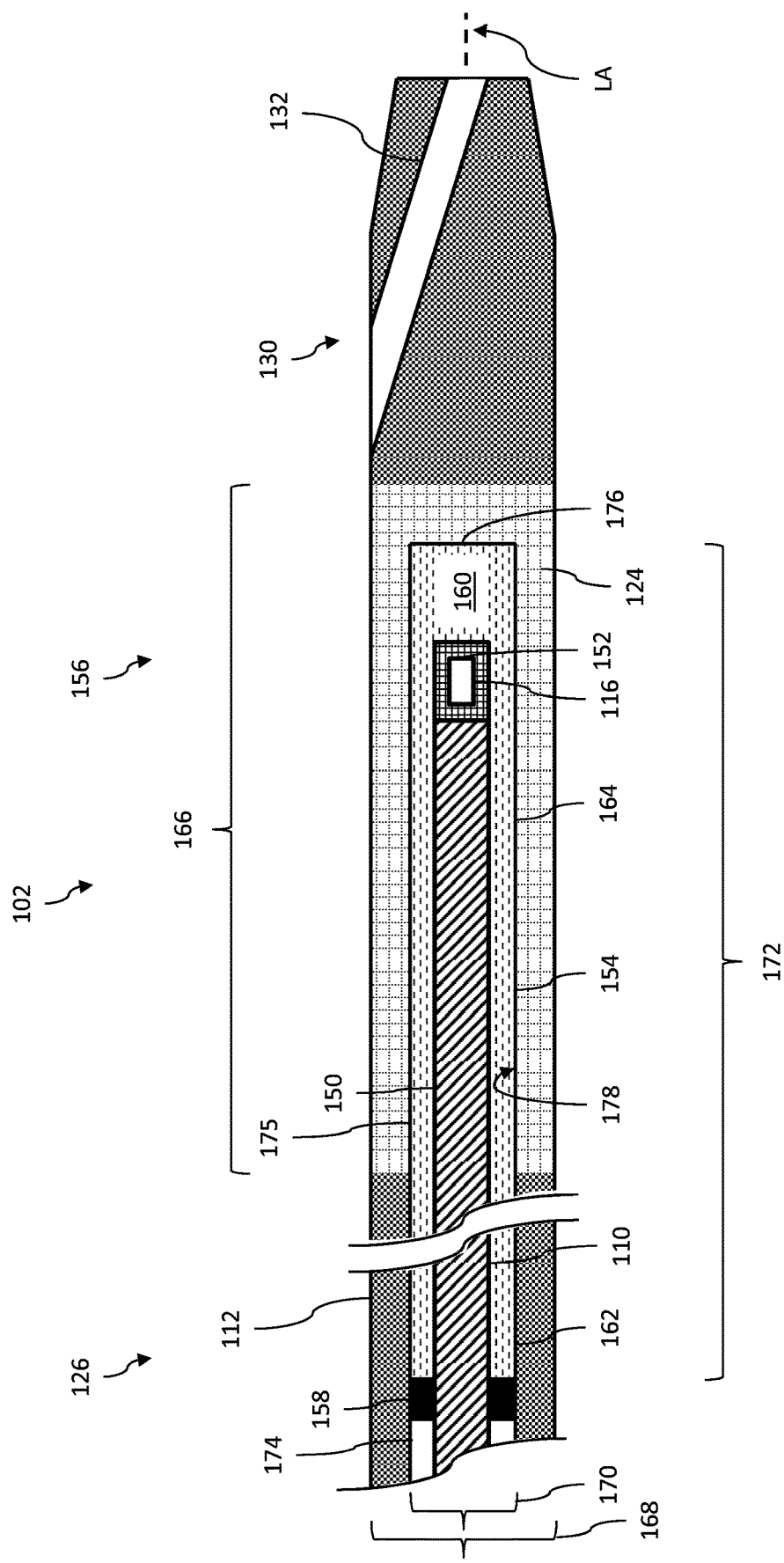
FIG. 3 is a cross-sectional side view of an intravascular device, including a rapid exchange port, showing a filling captively held within proximal and distal portions of a lumen according to an embodiment of the present disclosure.

Referring now to FIG. 3, shown therein is a cross-sectional side view of the rotational IVUS catheter 102. Generally, the catheter 102 includes the sheath or flexible elongate member 112, the drive cable 150 positioned with the lumen 154 of the flexible elongate member 112, the proximal shaft 126, the distal shaft 156, the acoustically transparent window 124, a sealing element 158, and a filling 160. FIG. 3 includes various components that are similar to those described with reference to other Figures in this disclosure, and description of the components will not be repeated here.

The lumen 154 can be described as an imaging core lumen because the imaging core 110 is disposed therein. The lumen 154 can also be described as a central lumen because, as shown in the FIG. 3, the lumen 154 is aligned with a central or longitudinal axis LA of the catheter 102. In other embodiments, the lumen 154 can be offset from the longitudinal axis LA. The lumen 154 extends along a majority of the working length (e.g., the length that is insertable into a patient's vasculature) of the flexible elongate member 112. In that regard, the working length of the flexible elongate member 112 and/or the length of the lumen 154 can be between approximately 50 cm and approximately 200 cm, between approximately 75 cm and approximately 200 cm, and between approximately 100 cm and approximately 200 cm, including values such as 90 cm, 135 cm, 150 cm, and/or other suitable values both larger and smaller. The outer diameter 168 of the flexible elongate member 112 can be any suitable value between approximately 0.020 in and approximately 0.125 in, between approximately 0.025 in and approximately 0.110 in, and between approximately 0.030 in and approximately 0.075 in, and/or other values both larger and smaller. The diameter of the lumen 170 can be any suitable value between approximately 0.010 in and approximately 0.10, between approximately 0.010 in and approximately 0.075 in, between approximately 0.010 in and 0.050 in, and/or other values both larger and smaller. In that regard, the outer diameter 168 of the proximal shaft 126 can be larger or smaller than the outer diameter of the distal shaft 156 and vice versa. The lumen 154 of the flexible elongate member 112 has a proximal portion 162 and a distal portion 164. In that regard, the diameter 170 of the proximal portion 162 of the lumen 154 can be larger or smaller than the diameter of the distal portion 164 and vice versa.

The drive cable 150 is configured to spin or rotate about the longitudinal axis LA of the catheter 102. The drive cable 150 is disposed within the lumen 154 such that the transducer 152 is positioned within the distal portion 164 of the lumen 154. The transducer 152 is also positioned within the length 166 of the acoustically transparent window 124. In that regard, the length 166 of the window 124 can be between approximately 1 cm and approximately 30 cm, between approximately 1 cm and approximately 20 cm, and between approximately 1 cm and approximately 15 cm, including values such as 10 cm, 12 cm, 15 cm, and/or other suitable values both larger and smaller. The length 166 of the window may be greater than or equal to the length of a pullback (e.g., during the IVUS imaging procedure).

The filling 160 is disposed within the lumen 154. For example, the filling 160 fills the lumen 154 such that the transducer 152, which is also disposed within the lumen 154, is surrounded by the filling 160. The filling 160 facilitates transmission of ultrasound signals from the transducer 152 and receipt of ultrasound echoes at the transducer. For example, the refractive index of the filling 160 can be approximately equal to the refractive index of blood. As described herein, the window 124 may be formed of a material that minimizes unintentional attenuation, reflection, or refraction. Accordingly, waves associated with ultrasound signals pass through the transition between the filling 160, the window 124, and blood within the patient's vasculature without being bent or curved in a manner that degrades the IVUS image. In some embodiments, the acoustical characteristics of the filling 160 may enhance the ultrasound signal, such as by focusing and/or otherwise modifying the waves associated with the ultrasound signals to improve the IVUS image.

The filling 160 can be biocompatible and/or ultrasound compatible. In various embodiments, the filling 160 can be a solid, a liquid, a polymer, a gel, other suitable material(s), and/or combinations thereof. For example, the filling 160 can be a saline, ultrasound gel, etc. In some embodiments, the filling is a solid, such as a powder, or a polymer that has a melting point similar to that of normal human body temperature. In such embodiments, the filling may transition from a solid to a liquid or from a crystalline/semi-crystalline phase to an amorphous solid phase when the catheter 102 is inserted into the patient's vasculature. The filling 160 may also provide lubrication for drive cable 150 as it rotates within the lumen 154.

In the embodiment of FIG. 3, the filling 160 is disposed within both the proximal and distal portions 162,164 of the lumen 154. In that regard, the filling 160 may occupy a length 172 similar to that of the total length of the lumen 154 and/or the working distance of the flexible elongate member 112. Thus, the length 172 of the lumen 154 that is filled with the filling 160 can be between approximately 50 cm and approximately 200 cm, between approximately 75 cm and approximately 200 cm, and between approximately 100 cm and approximately 200 cm, including values such as 90 cm, 135 cm, 150 cm, and/or other suitable values both larger and smaller. In some embodiments, the filling 160 may occupy the lumen 154 from the telescope 122 (e.g., at a proximal end of the lumen 154) and extend distally to a distal end 176 of the lumen 154. In other embodiments, the lumen 154 includes an unfilled section 174 that is proximate to the telescope 122. In such embodiments, the filling 160 does not occupy a proximal-most portion of the lumen 154. Thus, the filling 160 may be disposed within some parts (e.g., more distal parts) of the proximal portion 162 and not others (e.g., more proximal parts). In some embodiments, the unfilled section 174 may be the telescope 122 and/or the hub 118. The entire length of the drive cable 150 or portions thereof extending through the unfilled section 174 may be coated with a lubricant to facilitate smooth and uniform rotation of drive cable 150.

The filling 160 is captively held within the lumen 154. For example, during manufacture of the catheter 102, the filling 160 can be inserted into and sealed within the lumen 154. Thus, the manufacturer or distributor can ship the catheter 102 to a medical services provider, such as a hospital or other catheterization lab, with the filling 160 disposed within the lumen 154. In the illustrated embodiment, the sealing element 158 is disposed within the proximal portion 162 of the lumen 154. The sealing element 158 can be positioned at any point along length of the proximal portion 162 of the lumen 154. The sealing element 158 captively holds the filling 160 within the proximal and distal portions 162, 164 of the lumen 154. The sealing element 158 is configured to seal the filling 160 within the lumen 154 while simultaneously allowing the drive cable 150 to rotate. In that regard, the sealing element 158 may be circumferentially disposed around the drive cable 150 such that the drive cable extends through the sealing element. Within the drive cable 150 extending through the sealing element 158, the filling 160 is sealed within the lumen 154. The sealing element 158 may be in contact with the drive cable 150 and a wall 178 of the lumen 154. In some embodiments, the sealing element 158 may be annularly-shaped, ring-shaped, and/or donut-shaped. An inner surface of the sealing element 158 (e.g. the surface of the sealing element in contact with the drive cable 150) and/or an outer surface of the drive cable in contact with the sealing may be lubricated to facilitate smooth and uniform rotation of the drive cable. In various embodiments, the sealing element 158 may be an o-ring, a bearing, and/or other suitable components. Generally, the sealing element 158 may be formed of any suitable material including a metal, such as stainless steel, chrome steel, carbon alloy, etc., or a plastic, such as a polymer or elastomer, etc. As described herein, the hub 118 and/or the telescope 112 may include sealing and/or bearing component(s). In some embodiments, the sealing element 158 within the lumen 154 is provided in addition to any other sealing and/or bearing component(s) of the catheter 102. In such embodiments, the sealing element 158 is positioned distally of the proximal end of the flexible elongate member 112 (e.g., between the unfilled section 174 and the filled section 175). In other embodiments, the sealing element 158 is the sealing and/or bearing component of the hub 118 and/or the telescope 112.

The user can use the catheter 102 in an imaging procedure without flushing the lumen 154 (e.g., filing the lumen with a fluid) because the proximal and distal portions 162, 164 of the lumen 154 already contain the filling 160. In that regard, the user can remove the catheter 102 from its sterile packaging, connect the hub 118 to the PIM and/or rotational pullback device 104 (FIG. 1), insert the catheter 102 into the patient's vasculature, and collect ultrasound data, e.g., based on a workflow generated by the console 106 and/or displayed on the monitor 108. High quality IVUS images of the vasculature, based on the collected ultrasound data, are generated by the console 106 and displayed on the monitor 108. According to an aspect of the present disclosure, these and other steps may be performed without flushing the lumen 154 to remove air bubbles.

Figure 4:
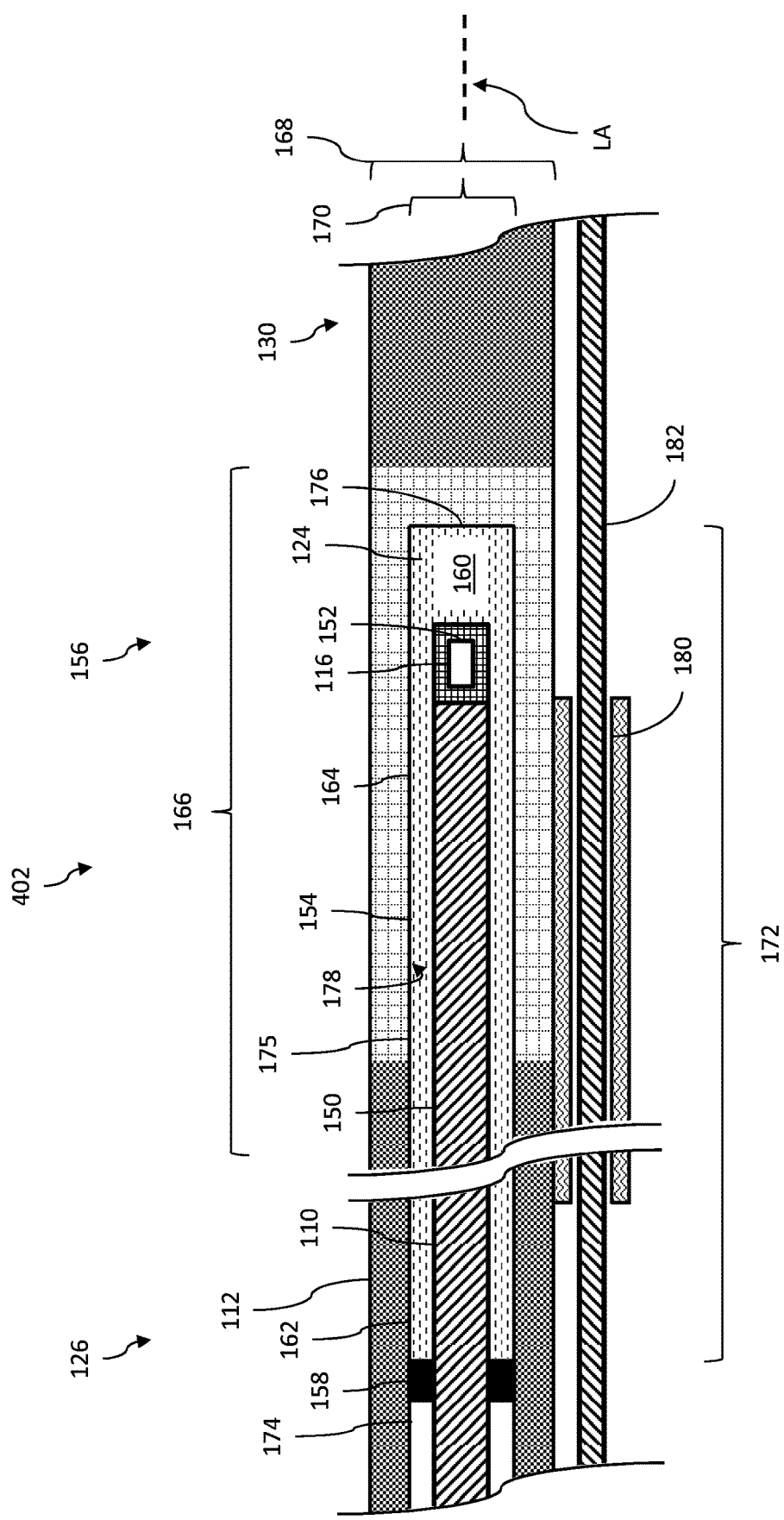
FIG. 4 is a cross-sectional side view of an intravascular device similar to that of FIG. 3 but including a monorail guidewire lumen in lieu of a rapid exchange port according to an embodiment of the present disclosure.

Referring now to FIG. 4, shown therein is a cross-sectional side view of a rotational IVUS catheter 402. FIG. 4 includes various components that are similar to those described with reference to other Figures in this disclosure, and description of the components will not be repeated here. In particular, the catheter 402 is similar to the catheter 102 (FIGS. 2 and 3) except that the catheter 402 includes a monorail lumen 180 that receives a guide wire 182 (as opposed to the rapid exchange port 132 illustrated in FIGS. 2 and 3). In that regard, the monorail lumen 180 is disposed parallel to the longitudinal axis LA of the catheter 102. For example, the monorail lumen 180 may be coupled to the flexible elongate member 112. As another example, the monorail lumen 180 may be integrally formed with the flexible elongate member 112. As shown in FIGS. 2-4, the teachings of the present disclosure may be implemented in intravascular devices with rapid exchange or monorail configurations.

Figure 5:
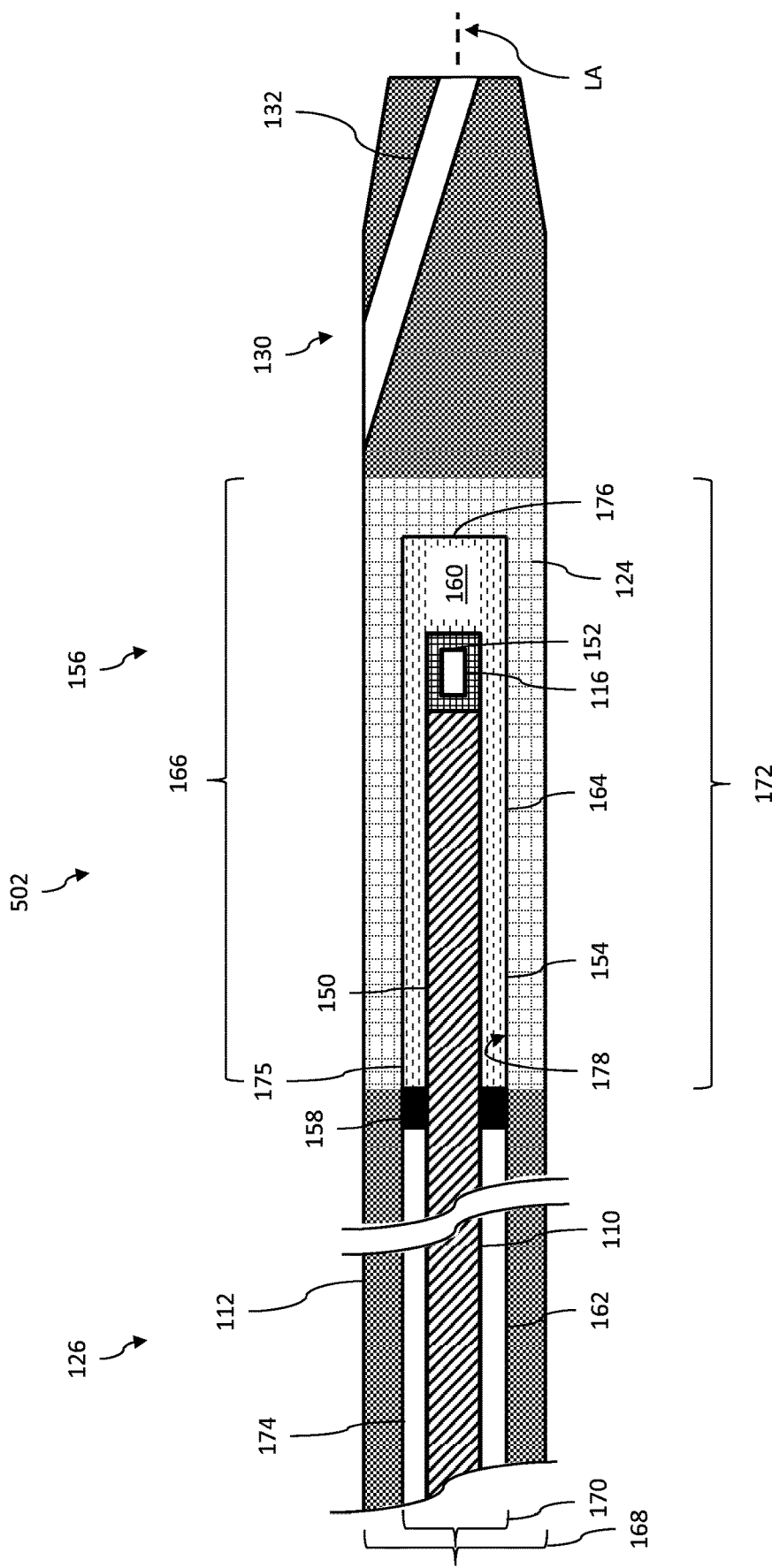
FIG. 5 is a cross-sectional side view of an intravascular device showing a filling captively held within a distal portion of a lumen according to an embodiment of the present disclosure.

Referring now to FIG. 5, shown therein is a cross-sectional side view of a rotational IVUS catheter 502. FIG. 5 includes various components that are similar to those described with reference to other Figures in this disclosure, and description of the components will not be repeated here. In particular, the catheter 502 is similar to the catheter 102 (FIG. 3) except that filling 160 in the catheter 502 is captively held within the distal portion 164 of the lumen 154. That is, the filled section 175 of the lumen 154 includes the distal portion 164. The unfilled section 174 of the lumen 154 includes portions of the lumen 154 that are proximal to the distal portion 164. Because the transducer 152, coupled to the drive cable 150, is also positioned within the distal portion 164 of the lumen 154, the filling 160 surrounds the transducer 152 and facilitates the transmission and reception of ultrasound signals. In the illustrated embodiment, the length 172 of the lumen 154 that is filled with the filling 160 is approximately equal to the length 166 of the acoustically transparent window 124. In other embodiments, the length 172 may be larger or smaller than the length 166. The sealing element 158 is positioned within the distal portion 164 of the lumen 154 to seal the filling 160 while allowing the drive cable 150 to rotate. The sealing element 158 can be positioned at any point along the length of the distal portion 164 of the lumen 154 while the transducer 152 is surrounded by the filling 160. The length 172 of the portion of the lumen 154 filled with the filling 160 may be greater than or equal to the length of a pullback (e.g., during the IVUS imaging procedure). The sealing element 158 can positioned between the proximal portion 162 and the distal portion 164 of the lumen 154. As described herein, the entire length of the drive cable 150 or portions thereof extending through the unfilled section 174 and/or the sealing element 158 may be coated with a lubricant to facilitate smooth and uniform rotation of drive cable 150. The user can use the catheter 502 in an imaging procedure without flushing the lumen 154 (e.g., filing the lumen with a fluid) because the distal portion 164 of the lumen 154 already contains the filling 160.

Figure 6:
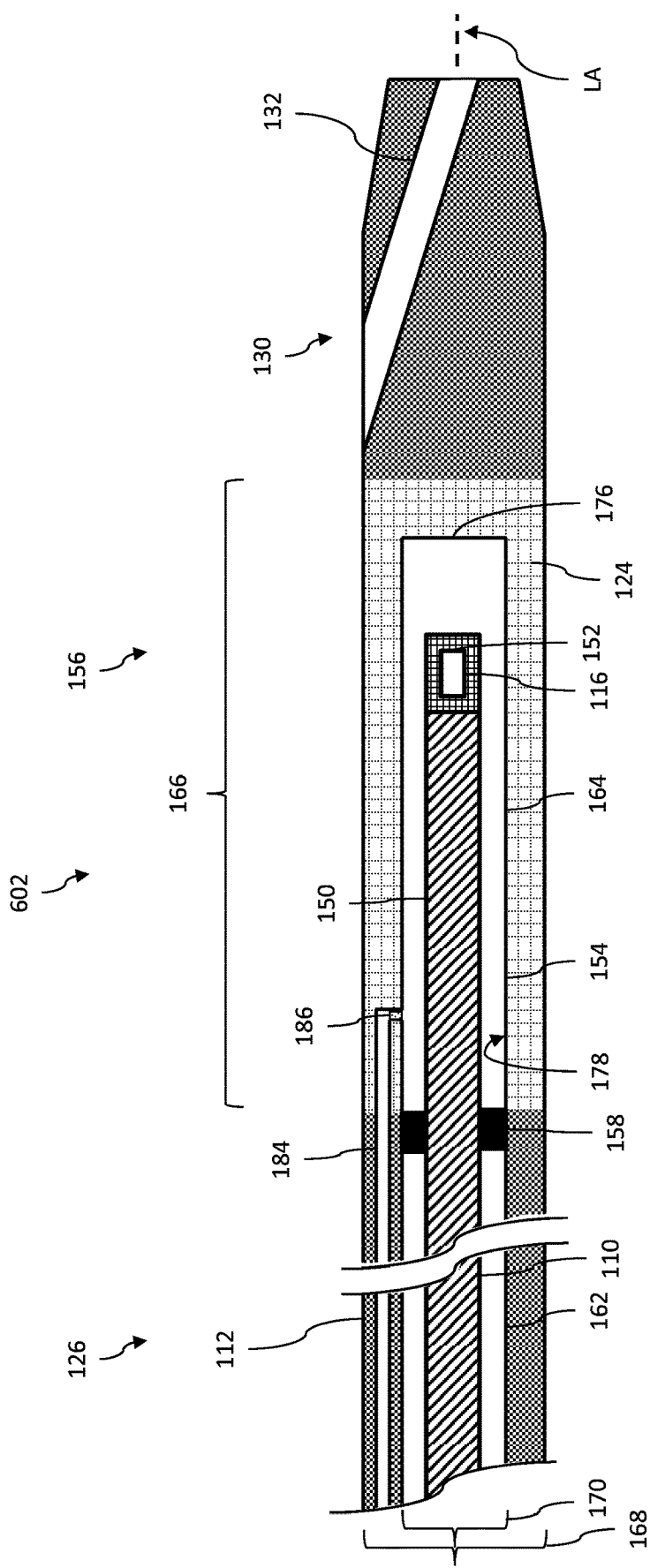
FIG. 6 is a cross-sectional side view of an intravascular device having first and second lumens according to an embodiment of the present disclosure.

Referring now to FIG. 6, shown therein is a cross-sectional side view of a rotational IVUS catheter 602. FIG. 6 includes various components that are similar to those described with reference to other Figures in this disclosure, and description of the components will not be repeated here. The sealing element 158 is disposed within the lumen 154 between the proximal portion 162 and the distal portion 164. With the drive cable 150 extending through the sealing element 158, the proximal and distal portions 162, 164 are fluidly isolated or separated from one another. The drive cable 150 is configured to rotate within the lumen 154.

The catheter 602 includes a lumen 184 in fluid communication with the distal portion 164 of the lumen 154. The lumen 184 is disposed within a side wall of the flexible elongate member 102. In the illustrated embodiment, the lumen 184 extends from the proximal portion of flexible elongate member 112 to the distal portion 164. In use, a user may introduce a fluid or other filling that facilitates transmission and receipt of ultrasound signals into the lumen 184 to fill the distal portion 164 of the lumen 154. For example, the lumen 184 can be in fluid communication with the flush port 120 (FIG. 2). The user may inject fluid or other filling into the flush port 120, and the fluid may travel through the lumen 184 into the distal portion 164 of the lumen 154. The transducer 152 is surrounded by the fluid when the distal portion 164 of the lumen 154 is filled with the fluid. In the illustrated embodiment, the proximal portion 162 of the lumen 154 does not include a filling. As described herein, the entire length of the drive cable 150 or portions thereof extending through the portion 162 (e.g., the unfilled section) of the lumen 154 and/or the sealing element 158 may be coated with a lubricant to facilitate smooth and uniform rotation of drive cable 150. In different embodiments, the size of the lumen 184 may vary such that a diameter of the lumen 184 is, for example, smaller than, the same size as, or larger than the diameter of the lumen 154.

The sealing element 158 is positioned relative the drive cable 150 to permit rotation of the drive cable and to hold the fluid or other filling captive within the distal portion 164 of the lumen 154. The fluid may also be held captive within the distal portion 164 by a sealing element 186 disposed within the lumen 184. In some embodiments, the sealing element 186 is a check valve that allows fluid to flow into the distal portion 164 but does not permit fluid to flow out of the distal portion. In other embodiments, the sealing element 186 is a plug that is inserted into the lumen 184 to prevent the fluid within the distal portion 164 and/or the lumen 184 from leaking. While the sealing element 186 is positioned adjacent to the proximal portion 164 in the illustrated embodiment, it is understood that the sealing element 186 may be positioned at any point along the length of the lumen 184 (e.g., at a proximal portion of the flexible elongate member 112, at or near the flush port 120, etc.). In use, air bubbles that may surround the transducer 152 can be eliminated by filling the distal portion 164 (as opposed to the entire length of the lumen 164) with fluid. Filling only the distal portion 164 (and not the entire length of the lumen 154) may allow for faster and more efficient setup for the IVUS imaging procedure.

Figure 7:
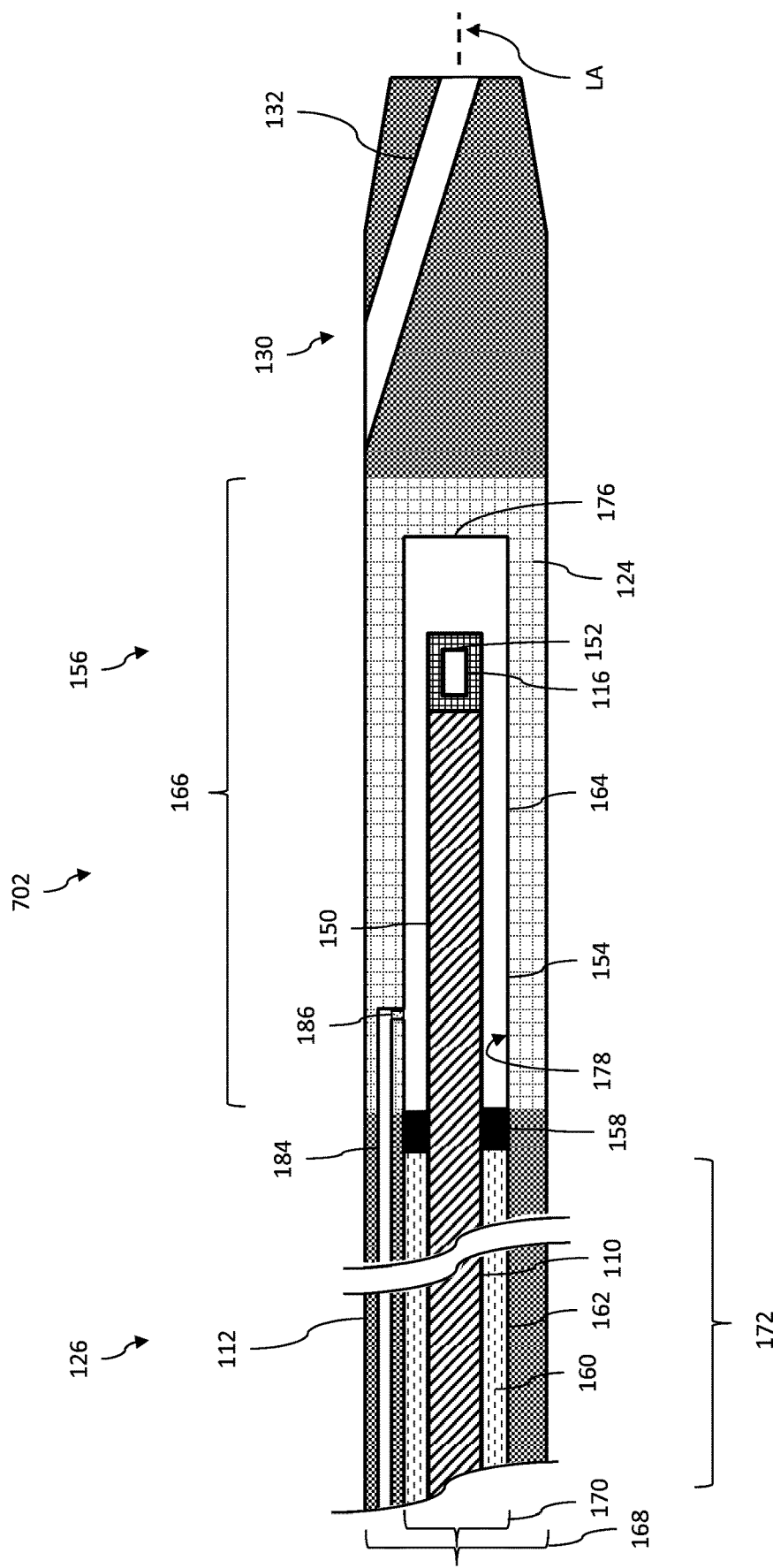
FIG. 7 is a cross-sectional side view of an intravascular device similar to that of FIG. 6 but including a filling captively held within a distal portion of a lumen according to an embodiment of the present disclosure.

Referring now to FIG. 7, shown therein is a cross-sectional side view of a rotational IVUS catheter 702. FIG. 7 includes various components that are similar to those described with reference to other Figures in this disclosure, and description of the components will not be repeated here. In particular, the catheter 702 is similar to the catheter 602 (FIG. 6) except that the filling 160 is captively held within the proximal portion 162 of the lumen 154 (as opposed to the proximal portion 162 not including the filling). In that regard, the sealing element 158 seals the filling 160 within the proximal portion 162. The length 172 of the lumen 154 that is filled with the filling 160 may be approximately equal to a total length of the flexible elongate member 112 less the length 166 of the window 124 and the length of any portions of the catheter 702 distal to the window 124. The filling 160 provides lubrication to facilitate smooth and uniform rotation of the drive cable 150 within the lumen 154. In the illustrated embodiment, the filling 160 can extends proximally to and occupies a proximal-most portion of the lumen 154. At the proximal portion of the catheter 102, the hub 118 and/or the telescope 122 can fluidly seal the filling within the lumen 154. In other embodiments, a further sealing element is provided near the proximal-most portion of the lumen 154 (e.g., as shown in FIGS. 3 and 4) such at the filling 160 is sealed between the two sealing elements. In such embodiments, the filling 150 does not occupy the proximal-most portion of the lumen 154.

Figure 8:
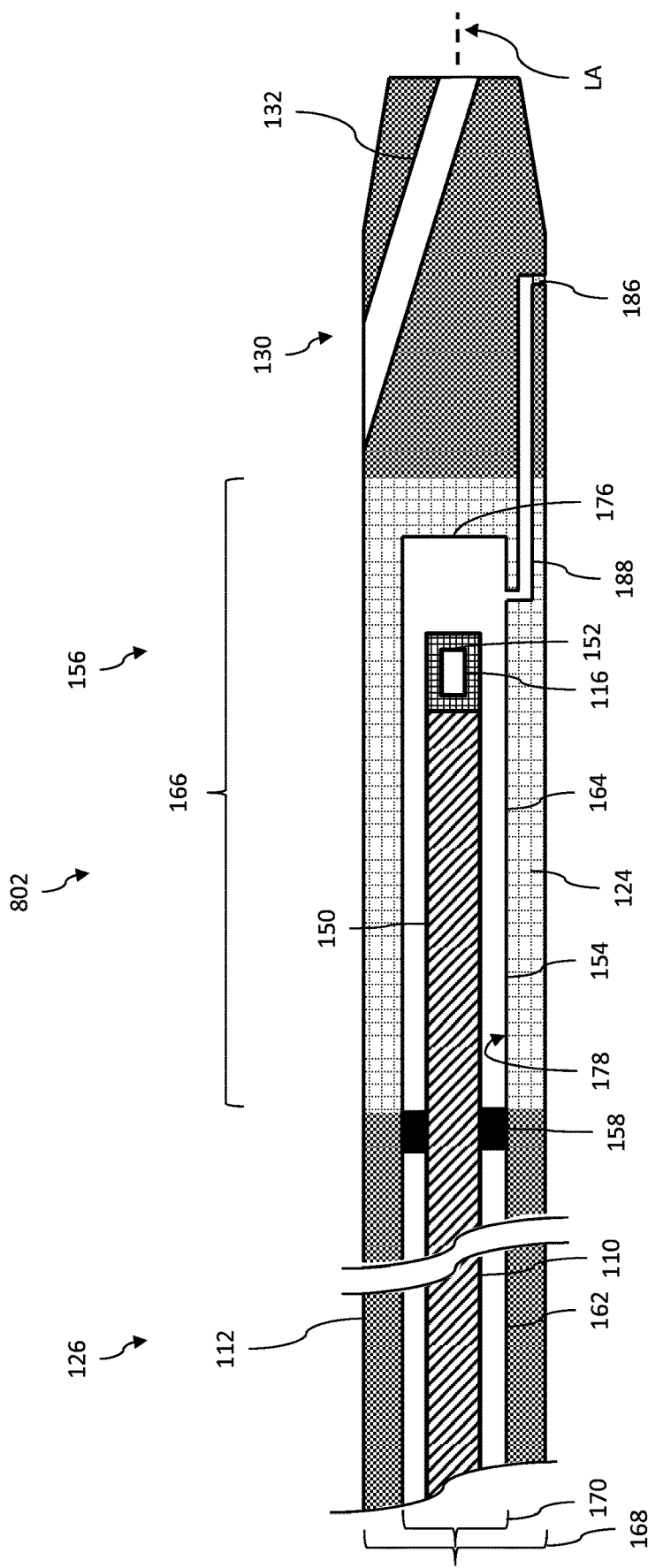
FIG. 8 is a cross-sectional side view of an intravascular device having first and second lumens according to another embodiment of the present disclosure.

Referring now to FIG. 8, shown therein is a cross-sectional side view of a rotational IVUS catheter 802. FIG. 8 includes various components that are similar to those described with reference to other Figures in this disclosure, and description of the components will not be repeated here. In particular, the catheter 802 is similar to the catheter 602 (FIG. 6) except that a lumen 188 extends from the distal portion 130 of the flexible elongate member 112 to the distal portion 164 of the lumen 154. In use, a user may introduce a fluid or other filling that facilitates transmission and receipt of ultrasound signals into the lumen 188 to fill the distal portion 164 of the lumen 154. For example, the user may inject a fluid into the lumen 188 and the distal portion 164. As another example, the user may immerse or soak at least the distal portion 130 of the flexible elongate member 112 in the fluid. The fluid may flow into the lumen 188 and the distal portion 164 by force of gravity or via capillary action, for example. The transducer 152 is surrounded by the fluid when the distal portion 164 of the lumen 154 is filled with the fluid. The sealing element 186 can be disposed at any point along the length of the lumen 188, including proximate to an outer surface of the catheter 102, as shown in the illustrated embodiment. The sealing element 186, such as a plug or check valve, along with the sealing element 158 captively holds fluid within the distal portion 164 and/or the lumen 188.

Figure 9:
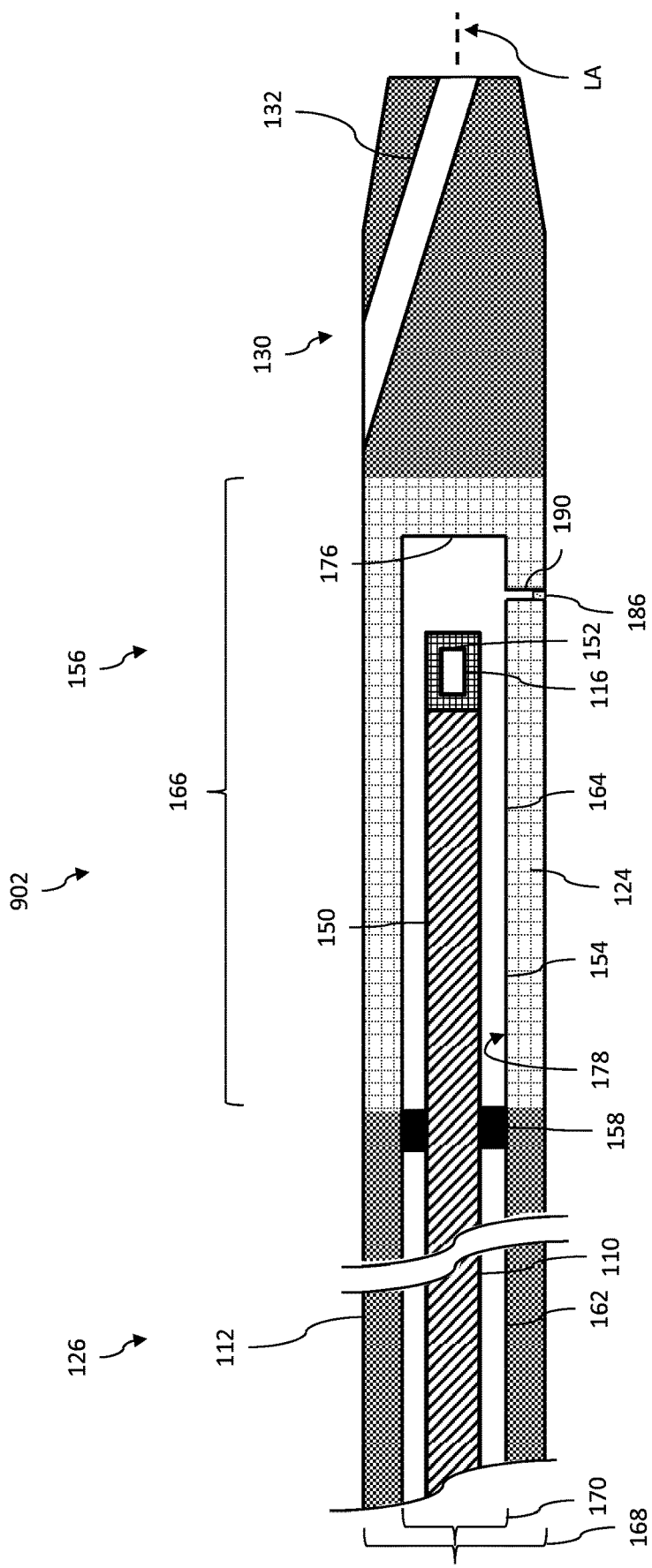
FIG. 9 is a cross-sectional side view of an intravascular device having first and second lumens according to another embodiment of the present disclosure.

Referring now to FIG. 9, shown therein is a cross-sectional side view of a rotational IVUS catheter 902. FIG. 9 includes various components that are similar to those described with reference to other Figures in this disclosure, and description of the components will not be repeated here. In particular, the catheter 902 is similar to the catheter 602 (FIG. 6) except that a lumen 190 extends from the acoustically transparent window 124 to the distal portion 164 of the lumen 154. In use, a user may introduce a fluid or other filling that facilitates transmission and receipt of ultrasound signals into the lumen 190 to fill the distal portion 164 of the lumen 154. For example, the user may inject a fluid into the lumen 190 and the distal portion 164. As another example, the user may immerse or soak at least the distal portion 130 of the flexible elongate member 112 in the fluid. The fluid may flow into the lumen 190 and the distal portion 164 by force of gravity or via capillary action, for example. The transducer 152 is surrounded by the fluid when the distal portion 164 of the lumen 154 is filled with the fluid. The sealing element 186 can be disposed at any point along the length of the lumen 190, including proximate to an outer surface of the catheter 102, as shown in the illustrated embodiment. The sealing element 186, such as a plug or check valve, along with the sealing element 158 captively holds fluid within the distal portion 164 and/or the lumen 190.

Figure 10:
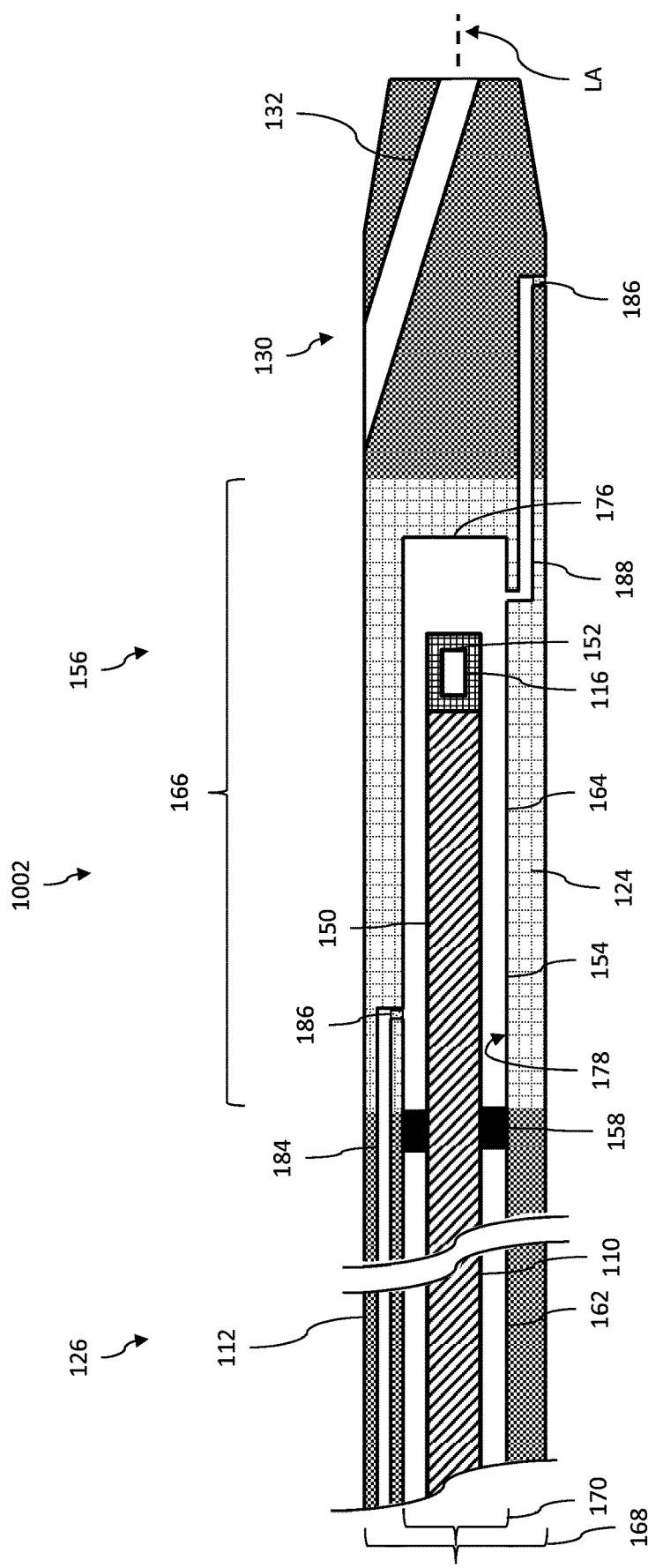
FIG. 10 is a cross-sectional side view of an intravascular device having first, second, and third lumens according to an embodiment of the present disclosure.

Referring now to FIG. 10, shown therein is a cross-sectional side view of a rotational IVUS catheter 1002. FIG. 10 includes various components that are similar to those described with reference to other Figures in this disclosure, and description of the components will not be repeated here. In particular, the catheter 1002 is similar to the catheter 602 (FIG. 6) except that the lumen 184 and the lumen 188 are in fluid communication with the distal portion 164 of the lumen 154. In use, a user may introduce a fluid or other filling that facilitates transmission and receipt of ultrasound signals into the lumen 184 to fill the distal portion 164 of the lumen 154 by providing suction at the lumen 188 (or vice versa). In that regard, the proximal portion and/or the distal portion 130 of the flexible elongate member 112 may be immersed or soaked in the fluid. By providing suction at either one of the lumens 184, 188, the fluid can travel through the other one of the lumens 184, 188 and into the distal portion 164 of the lumen 154. The transducer 152 is surrounded by the fluid when the distal portion 164 of the lumen 154 is filled with the fluid. The sealing elements 186 can be disposed at any point along the length of the lumens 184, 188, including proximate to an outer surface of the catheter 102, as shown in the illustrated embodiment. The sealing elements 186, such as plugs or check valves, along with the sealing element 158, captively hold fluid within the distal portion 164, the lumen 184, and/or the lumen 186.

Figure 11:
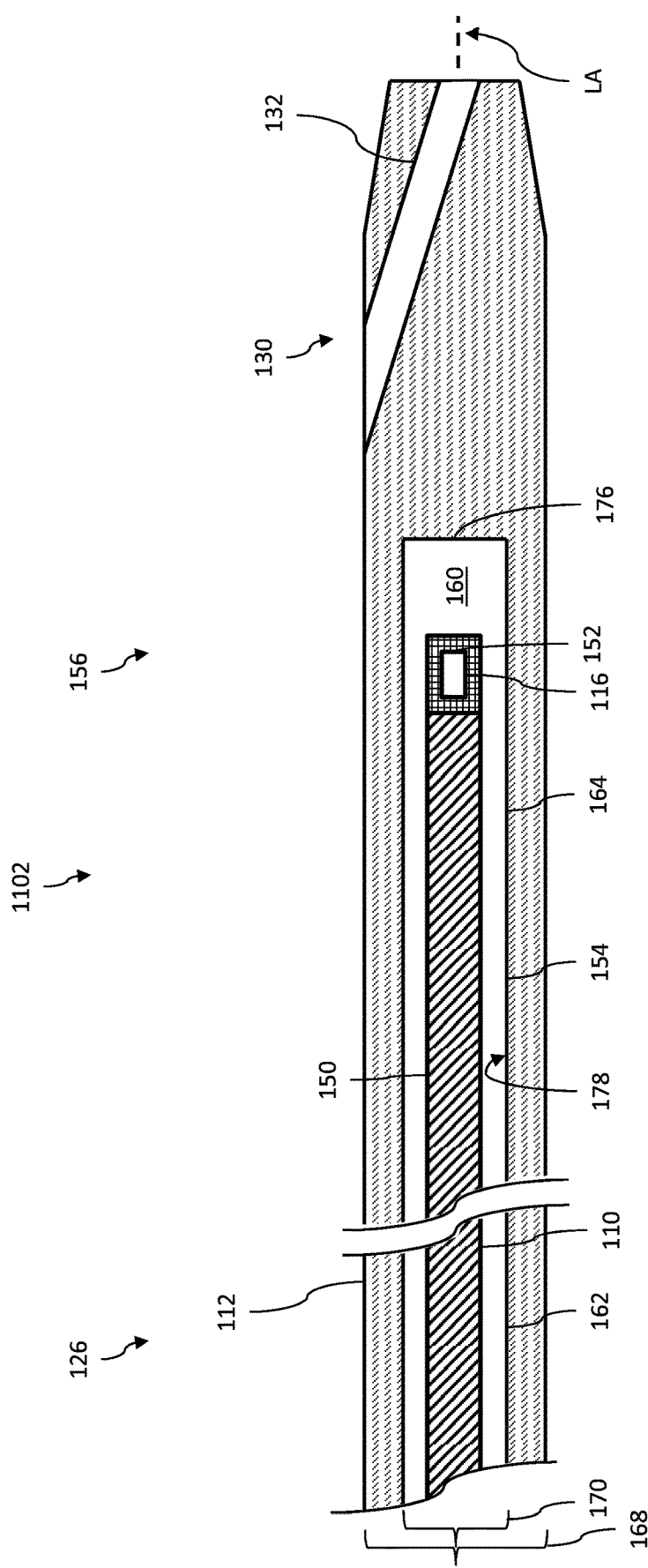
FIG. 11 is a cross-sectional side view of an intravascular device formed of a permeable material according to an embodiment of the present disclosure.

Referring now to FIG. 11, shown therein is a cross-sectional side view of a rotational IVUS catheter 1102. FIG. 11 includes various components that are similar to those described with reference to other Figures in this disclosure, and description of the components will not be repeated here. In particular, the catheter 1102 is similar to the catheter 102 (FIGS. 3 and 4) except that the flexible elongate member 112 is formed of a material that is permeable to a fluid or other filling that facilitates transmission and receipt of ultrasound signals. In use, a user may introduce a fluid or other filling into the distal portion 164 of the lumen 154 by immersing or soaking all or a portion of the flexible elongate member 112 in the fluid. In some embodiments, the material forming the flexible elongate member 112 may be configured to allow fluid to flow into the material (and into the lumen 154) and restrict the fluid flow out of the material. The transducer 152 is surrounded by the fluid when the distal portion 164 of the lumen 154 is filled with the fluid. At the proximal portion of the catheter 102, the hub 118 and/or the telescope 122 can fluidly seal the filling within the lumen 154. In other embodiments, a further sealing element is provided near the proximal-most portion of the lumen 154 (e.g., as shown in FIGS. 3 and 4). In some embodiments, the material forming the flexible elongate member 112 may be acoustically transparent such that it readily conducts ultrasound waves between the transducer 152 and the vessel tissue with minimal attenuation, reflection, or refraction. By filling the lumen 154 with the fluid by soaking or immersing the flexible elongate member 112, the catheter 1102 need not include components related to conventional flushing (e.g., the flush port 120 of FIG. 2). This can allow the manufacturer greater flexibility in designing the catheter 1102.

Figure 12:
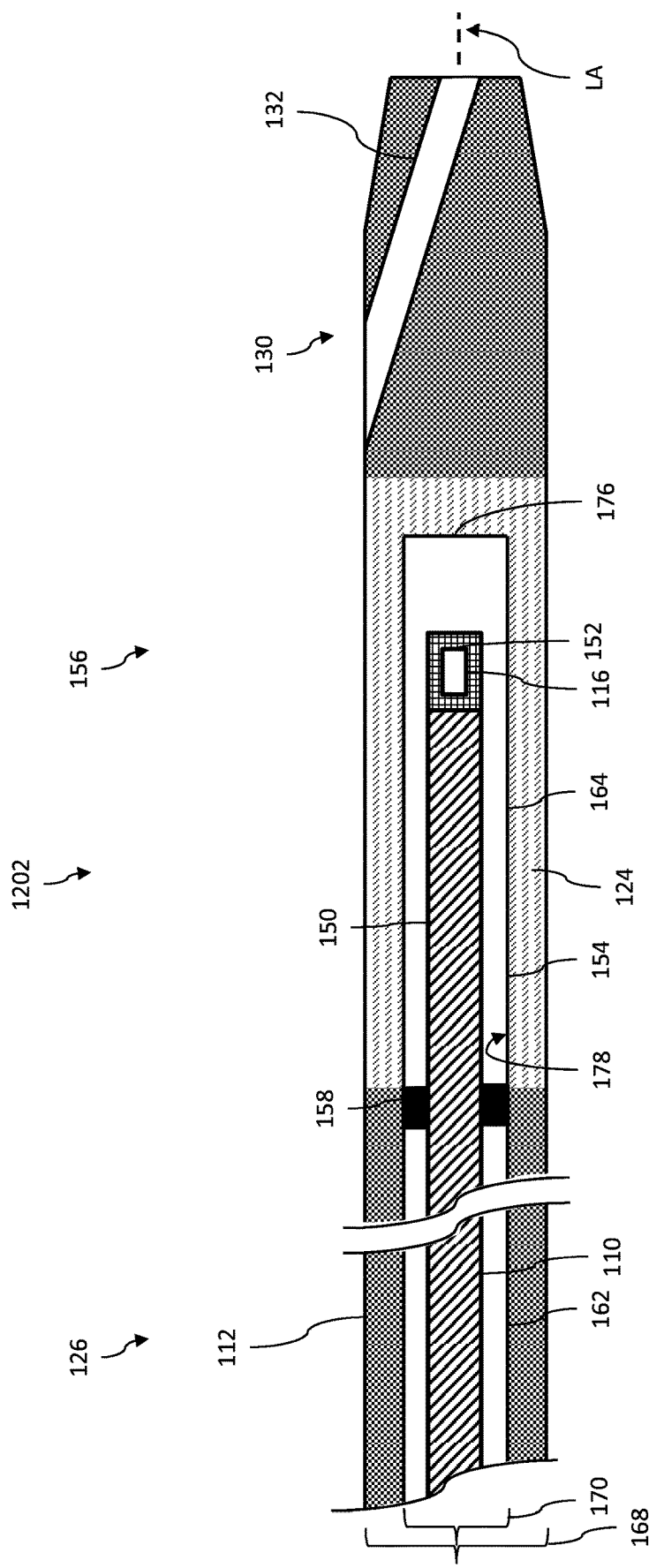
FIG. 12 is a cross-sectional side view of an intravascular device of which a portion is formed of a permeable material according to an embodiment of the present disclosure.

Referring now to FIG. 1202, shown therein is a cross-sectional side view of a rotational IVUS catheter 1202. FIG. 12 includes various components that are similar to those described with reference to other Figures in this disclosure, and description of the components will not be repeated here. In particular, the catheter 1202 is similar to the catheter 1102 (FIG. 11) except that only a portion of the flexible elongate member 112 is formed the material that is permeable to a fluid or other filling that facilitates transmission and receipt of ultrasound signals. In the illustrated embodiment, the portion of the flexible elongate member 112 that is aligned with the distal portion 164 of the lumen 154 is formed of the permeable material. In use, a user may introduce a fluid or other filling into the distal portion 164 of the lumen 154 by immersing or soaking at least the portion of the flexible elongate member 112 formed of the permeable material in the fluid. The transducer 152 is surrounded by the fluid when the distal portion 164 of the lumen 154 is filled with the fluid. The sealing element 158, along with the one-way permeable material, captively holds the fluid within distal portion 164 while allowing the drive cable 150 to rotate within the lumen 154. In the illustrated embodiment, the permeable material forms the acoustically transparent window 124.

Figure 13:
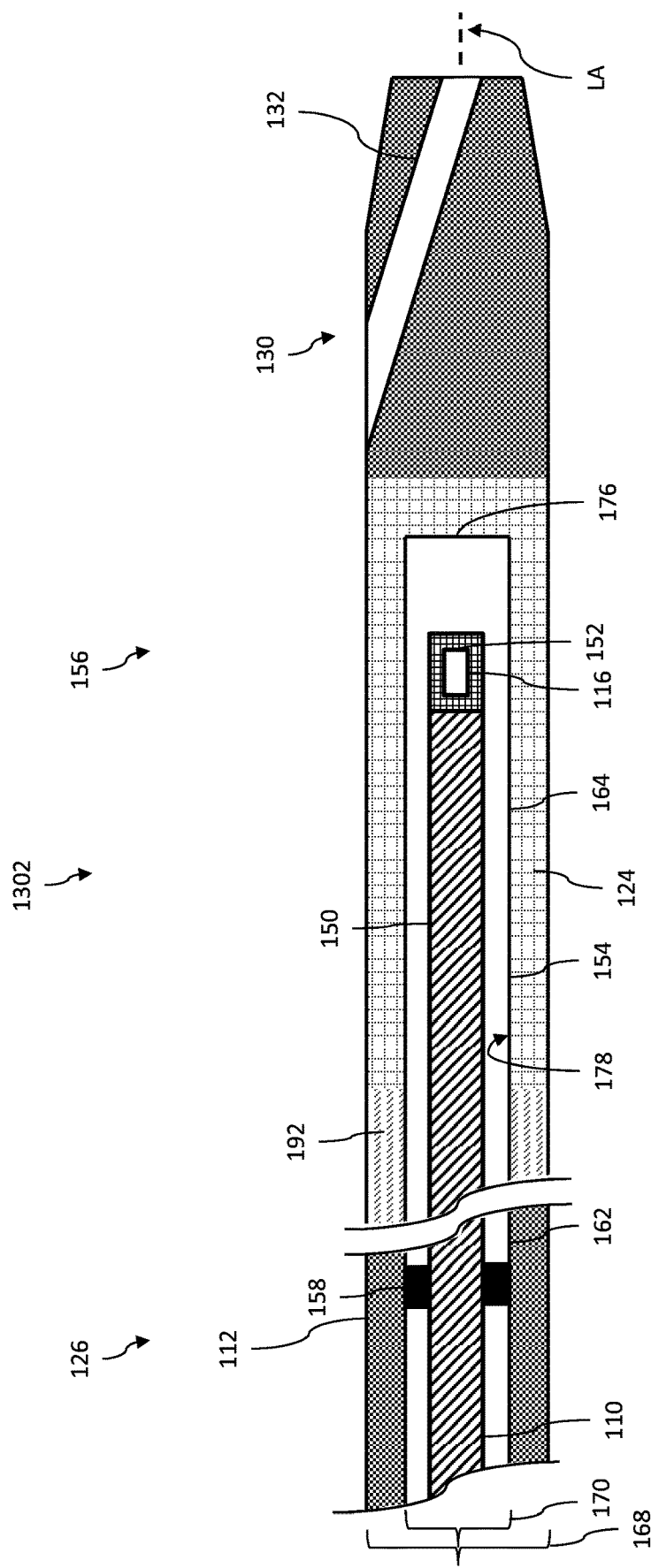
FIG. 13 is a cross-sectional side view of an intravascular device of which a portion is formed of a permeable material according to another embodiment of the present disclosure.

Referring now to FIG. 13, shown therein is a cross-sectional side view of a rotational IVUS catheter 1302. FIG. 13 includes various components that are similar to those described with reference to other Figures in this disclosure, and description of the components will not be repeated here. In particular, the catheter 1302 is similar to the catheter 1202 (FIG. 12) except that a section 192 of the flexible elongate member 112 is formed the material that is permeable to a fluid or other filling that facilitates transmission and receipt of ultrasound signals. In the illustrated embodiment, the section 192 is at least partially aligned the proximal portion 162 of the lumen 154. In different embodiments, the section 192 may have varying lengths such that it is partially or fully aligned with the proximal portion 162 of the lumen 154. In use, a user may introduce a fluid or other filling into the distal portion 164 of the lumen 154 by immersing or soaking at least the section 192 of the flexible elongate member 112 in the fluid. The transducer 152 is surrounded by the fluid when the distal portion 164 of the lumen 154 is filled with the fluid. The sealing element 158, along with the one-way permeable material, captively holds the fluid within distal portion 164 while allowing the drive cable 150 to rotate within the lumen 154. As described herein, the window 124 can be composed of thin-walled plastic tubing fabricated from material(s) that readily conduct ultrasound waves between the transducer and the vessel tissue with minimal attenuation, reflection, or refraction.

Figure 14:
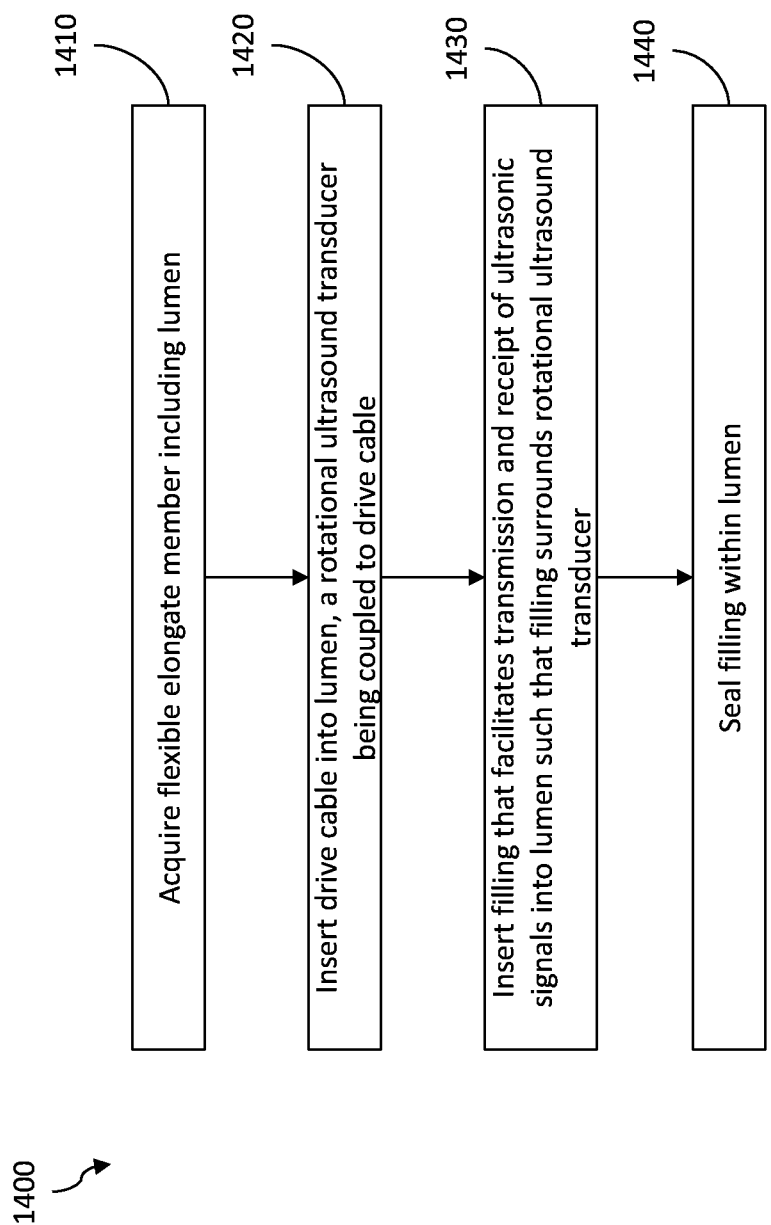
FIG. 14 is a flow diagram of a method of manufacturing an intravascular device according to an embodiment of the present disclosure.

FIG. 14 illustrates a flowchart of a method 1400 of a manufacturing an intravascular device. As illustrated, the method 1400 includes a number of enumerated steps, but implementations of the method 1400 may include additional steps before, after, and in between the enumerated steps. In some implementations, one or more of the enumerated steps may be omitted or performed in a different order. The steps of the method 1400 may be performed by an intravascular device manufacturer, for example.

At step 1410, the method 1400 includes acquiring a flexible elongate member having a lumen. In some embodiments, the flexible elongate member can be polymer tube (which may be coil-embedded or not). In that regard, the flexible elongate member can have different sections formed of different materials. For example, a distal section of the flexible elongate member may be acoustically transparent while a proximal section is not. Acquiring the flexible elongate member can include forming or manufacturing the flexible elongate member or procuring a flexible elongate member having the desired characteristics (e.g., length, flexibility, etc.).

At step 1420, the method 1400 includes inserting a drive cable into the lumen of the flexible elongate member. A rotational ultrasound transducer can be coupled to the distal end of the drive cable. Accordingly, in some embodiments, the method 1400 can include coupling the transducer to the drive cable. The flexible elongate member can include proximal opening through which the lumen is accessed. In the illustrated example of FIG. 3, for example, the distal end of the lumen of the flexible elongate member is sealed. Inserting the drive cable into the lumen can include threading the drive cable into the flexible elongate member, starting at the proximal opening and continuing along the length of the lumen. Inserting the drive cable into the lumen can include pulling the flexible elongate member onto the drive cable, starting at the proximal opening and continuing along the length of the lumen.

At step 1430, the method 1400 includes inserting a filling that facilitates transmission and receipt of ultrasonic signals into the lumen such that the filling surrounds rotational ultrasound transducer. In that regard, the filling, such as a solid, a liquid, a polymer, a gel, other suitable materials, and/or combinations thereof may be introduced into a proximal portion and/or a distal portion of the lumen. Inserting the filling can include injecting, pouring, and/or otherwise placing the filling within the lumen. The lumen can be accessed by the proximal opening of the flexible elongate member. In some embodiments, the order of steps 1420 and 1430 may be reversed. For example, the lumen of the flexible elongate member may be filled with the filling before the drive cable is inserted. The lumen may be filled to capacity and as the drive cable is inserted, the excess filling may be removed from the lumen. In some embodiments, the steps 1420 and 1430 may be combined. For example, all or a portion of the drive cable maybe coated, e.g., with a gel or a polymer and then inserted into the lumen of the flexible elongate member. In various embodiments, additional filling may be inserted into lumen to ensure that no air bubbles are within the distal portion of the lumen where the transducer is located.

In embodiments in which the flexible elongate member is wholly or partially formed of a material permeable to the filling, the inserting a filling includes positioning at least a portion (e.g., the permeable portion) of the flexible elongate member in the filling. The filling can permeate into the lumen such the filling surrounds the ultrasound transducer. In embodiments in which the flexible elongate member includes a further lumen in fluid communication with a distal portion of the lumen (e.g., where the ultrasound transducer is located), inserting the filling can include introducing the filling into the distal portion of the lumen via the further lumen. Introducing the filling into the distal portion via the further lumen can include injecting, pouring, and/or otherwise placing the filling within the distal portion via the further lumen. In some embodiments, at least a portion (e.g. the portion containing an opening of the further lumen) of the flexible elongate member may be soaked or immersed in the filling such that filling enters the further lumen by force of gravity or via capillary action. In some embodiments, another lumen in fluid communication with the distal portion of the lumen may be provided such that suction can be applied to one of the further lumen or the other lumen to draw the fluid into the distal portion via the one of the further lumen or the other lumen. A sealing element can be positioned between the distal and proximal portions of the lumen to isolate the distal and proximal portions. In that regard, the method 1400 can further include inserting the sealing element between the proximal and distal portions of the lumen.

At step 1440, the method 1400 includes sealing the filling within the lumen. For example, a mechanical component may be positioned within the lumen to prevent the filling from inadvertently being evacuated or leaking from the lumen (e.g., the distal portion of the lumen). If the filling were to leak, the ultrasound transducer may not be completely surrounded by the filling (e.g., circumferentially around the transducer and the entire axial distance between the transducer and the wall of the lumen), which may degrade IVUS image quality. In some embodiments, the sealing the filling can include positioning a sealing element around the drive cable. In that regard, the steps 1420 and 1440 can be combined in some embodiments. For example, the drive cable can be threaded through the sealing element prior to the drive cable being inserted into the flexible elongate member. Thus, as the drive cable is inserted into the lumen, the sealing element is also inserted into the lumen, surrounding the drive cable. In other embodiments, such as those with a further lumen in fluid communication with the distal portion of the lumen, sealing the filling can include introducing the filling into the distal portion via a check valve. The check valve can be disposed within the further lumen. The check valve seals the filling by permitting flow only into to the distal portion of the lumen. In still other embodiments, sealing the filling can include positioning a plug within further lumen to prevent backflow of the filing.

The method 1400 can include other suitable steps in different embodiments. For example, the method 1400 can include inserting the drive cable through a telescoping section at a proximal end of the flexible elongate member, inserting the drive cable through a hub at a proximal end of the flexible elongate member, coupling the flexible elongate member to the telescoping section and the hub, electrically coupling the transducer via wire(s), and/or other suitable steps to assemble the intravascular device.

While the present disclosure specifically refers to a catheter, it is understood that the features described herein may be implemented in guide wire, guide catheters, and/or other intravascular devices. Similarly, while the features of the present disclosure may be implemented with imaging modalities other than IVUS, include optical coherence tomography (OCT). As such, the housing 116 (FIG. 2) of an OCT catheter can include optical fiber(s) and optical imaging element(s) (e.g., mirrors, prisms, scanners, etc.). Aspects of the present disclosure may be implemented in intravascular devices adapted for use in the coronary or peripheral vasculature.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular imaging device, comprising:
    a flexible elongate member including a continuous side wall forming a lumen having a proximal portion and a distal portion;
    a drive cable disposed within the lumen such that an ultrasound transducer coupled to the drive cable is positioned within the distal portion of the lumen;
    a sealing element disposed within the lumen such that the sealing element and the side wall define a sealed compartment encompassing at least the distal portion of the lumen, wherein the sealing element fluidly isolates the sealed compartment; and
    a filling captively sealed within the sealed compartment and surrounding the ultrasound transducer for facilitating transmission and reception of ultrasound signals.

2. The intravascular imaging device of claim 1, wherein the drive cable extends through the sealing element.

3. The intravascular imaging device of claim 2, wherein the drive cable is configured to rotate within the lumen.

4. The intravascular imaging device of claim 3, wherein the sealing element comprises an o-ring or a bearing.

5. The intravascular imaging device of claim 4, wherein the filling comprises saline or ultrasound gel.

6. The intravascular imaging device of claim 1, wherein the sealed compartment encompasses the proximal and distal portions of the lumen.

7. The intravascular imaging device of claim 1, wherein the filling comprises a solid, a liquid, a polymer, or a gel.

8. The intravascular imaging device of claim 1,
    wherein at least a portion of the flexible elongate member comprises a material permeable to the filling, wherein the material is configured to allow the filling to flow into the lumen and restrict the filling from flowing out of the lumen.

9. The intravascular imaging device of claim 1, wherein a diameter of the sealed compartment is constant along a length of the sealed compartment.

10. An intravascular imaging device, comprising:
    a flexible elongate member including a side wall forming:
        a first lumen having a proximal portion and a distal portion; and
        a second lumen spaced from the first lumen;
    a first sealing element disposed within the first lumen between the proximal and distal portions such that the proximal and distal portions are not in fluid communication with one another, wherein the first sealing element is arranged within the first lumen such that the proximal portion of the first lumen extends proximally from the first sealing element and the distal portion of the first lumen extends distally from the first sealing element;
    a second sealing element disposed within the second lumen such that the side wall, the first sealing element, and the second sealing element define a sealed compartment encompassing at least the distal portion of the first lumen, wherein the sealing element fluidly isolates the sealed compartment;
    a filling captively sealed within the sealed compartment; and
    a drive cable disposed within the first lumen such that an ultrasound transducer coupled to the drive cable is positioned within the distal portion of the first lumen.

11. The intravascular imaging device of claim 10, wherein the drive cable is configured to rotate within the first lumen, and wherein the first sealing element is positioned relative the drive cable to permit rotation of the drive cable and to hold the filling captive within the distal portion of the first lumen.

12. The intravascular imaging device of claim 11, wherein the flexible elongate member comprises a proximal section and a distal section, wherein the second lumen extends from the proximal section of the flexible elongate member to the distal portion of the first lumen.

13. The intravascular imaging device of claim 11, wherein the flexible elongate member comprises a proximal section and a distal section, wherein the second lumen extends from the distal section of the flexible elongate member to the distal portion of the first lumen.

14. The intravascular imaging device of claim 11, wherein the flexible elongate member comprises an imaging window, and wherein the second lumen extends from the imaging window of the flexible elongate member to the distal portion of the first lumen.

15. The intravascular imaging device of claim 11, wherein the side wall of the flexible elongate member forms a third lumen spaced from the first lumen and the second lumen.

* * * * *